United States Patent [19]

Brouwer et al.

[11] 4,399,152
[45] Aug. 16, 1983

[54] SUBSTITUTED BENZOYL UREAS AS INSECTICIDES

[75] Inventors: Marius S. Brouwer; Arnoldus C. Grosscurt, both of Weesp, Netherlands

[73] Assignee: Duphar International B.V., Netherlands

[21] Appl. No.: 330,484

[22] Filed: Dec. 14, 1981

Related U.S. Application Data

[63] Continuation of Ser. No. 137,027, Apr. 3, 1980, abandoned.

[51] Int. Cl.³ .................... A01N 47/28; C07C 127/19; C07C 127/22
[52] U.S. Cl. ...................................... 424/322; 564/44
[58] Field of Search .................... 424/322; 564/44, 45, 564/47

[56] References Cited

U.S. PATENT DOCUMENTS

| | | | |
|---|---|---|---|
| 3,845,086 | 10/1974 | Marsh | 424/322 |
| 3,989,847 | 11/1976 | Wellinga et al. | 424/322 |
| 3,992,553 | 11/1976 | Sirrenberg et al. | 424/304 |
| 4,005,223 | 1/1977 | Sirrenberg et al. | 424/322 |
| 4,013,706 | 3/1977 | Anatol et al. | 260/471 C |
| 4,013,717 | 3/1977 | Wellinga et al. | 260/553 E |
| 4,041,177 | 8/1977 | Sirrenberg et al. | 424/322 |
| 4,068,002 | 1/1978 | Sirrenberg et al. | 424/322 |
| 4,085,226 | 4/1978 | Sirrenberg et al. | 424/322 |
| 4,089,975 | 5/1978 | Wade et al. | 424/322 |
| 4,101,575 | 7/1978 | Enders et al. | 424/322 |
| 4,133,956 | 1/1979 | Abdulla et al. | 544/336 |
| 4,139,636 | 2/1979 | Sirrenberg et al. | 424/322 |
| 4,150,160 | 4/1979 | Drabek et al. | 424/322 |
| 4,170,657 | 10/1979 | Rigterink | 564/44 |
| 4,194,005 | 3/1980 | Sirrenberg et al. | 424/304 |
| 4,277,499 | 7/1981 | Sirrenberg et al. | 424/322 |

FOREIGN PATENT DOCUMENTS

| | | | |
|---|---|---|---|
| 1203 | 4/1979 | European Pat. Off. | 424/322 |
| 4030 | 9/1979 | European Pat. Off. | 424/322 |
| 2726684 | 4/1979 | Fed. Rep. of Germany | 424/322 |
| 2801316 | 7/1979 | Fed. Rep. of Germany | 424/322 |

*Primary Examiner*—Douglas W. Robinson
*Attorney, Agent, or Firm*—Stevens, Davis, Miller & Mosher

[57] ABSTRACT

The invention relates to new benzoyl ureas of the formula

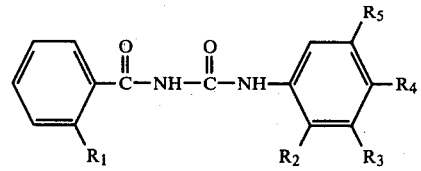

wherein $R_1$, $R_2$, $R_3$, $R_4$ and $R_5$ are hereafter defined. The invention also includes insecticidal compositions and the use thereof which contain the above compounds.

3 Claims, No Drawings

SUBSTITUTED BENZOYL UREAS AS INSECTICIDES

This is a continuation of application Ser. No. 137,027 filed Apr. 3, 1980, now abandoned.

The invention relates to new benzoyl ureas, to insecticidal compositions containing the new compounds, and to the use of these compositions for controlling insects. Benzoylureas having insecticidal properties are known e.g. from U.S. Pat. Nos. 3,748,356; 3,933,908; 3,989,842; 4,068,002; and 4,085,226.

The present invention provides, as new compounds, N-phenyl-N'-benzoylureas of the general formula

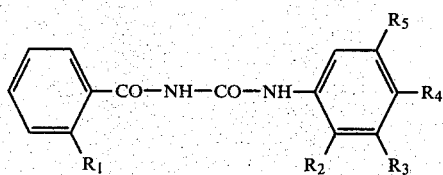

wherein $R_1$ is a halogen atom or a methyl group, $R_2$ and $R_5$ are equal or different and represent hydrogen atoms or chlorine atoms, $R_3$ is a hydrogen atom, a chlorine atom or a nitro group, and $R_4$ is a halogen atom, a nitro group, an alkoxy group having 1 to 8 carbon atoms, a trifluoromethyl group, a trifluoromethylsulphonyl group, an alkyl group having 1 to 6 carbon atoms, a phenoxy group, a 2,5-dichlorophenoxy group, a 4-chlorophenylthio group, a 4-chlorophenylsulphonyl group, or a mono-, di- or tricycloalkyl group having 5 to 12 carbon atoms, or wherein, if $R_2$, $R_3$ and $R_5$ all represent hydrogen atoms, $R_4$ is in addition a 2,4-dichlorophenoxy group, or wherein, if $R_1$ is a chlorine atom, $R_2$ is a hydrogen atom, and $R_3$ and $R_5$ both represent either hydrogen atoms or chlorine atoms, $R_4$ is in addition a 4-chlorophenoxy group;

with the understanding that $R_3$ and $R_4$ are not both chlorine atoms.

The new compounds of the present invention are effective insecticides and can generally be produced from relatively cheap raw materials.

Of the above-mentioned compounds particularly those compounds are excellently suitable which, in addition to a high insecticidal activity, have a wide activity spectrum, that is to say have a high activity against a large number of different insects, for example, caterpillars, larvae of flies and mosquitos, and larvae of beetles. These compounds are represented by the general formula

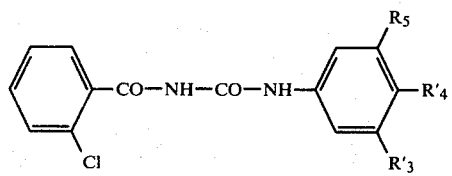

wherein $R_5$ and $R_3'$ both represent either hydrogen atoms or chlorine atoms, and, if $R_5$ and $R_3'$ both represent hydrogen atoms, $R_4'$ is a trifluoromethyl group, or, if $R_5$ and $R_3'$ both represent chlorine atoms, $R_4'$ is a phenoxy- or 4-chlorophenoxy group.

Insecticidally very effective compounds are:
(1) N-(2-chlorobenzoyl)-N'-(4-trifluoromethylphenyl)urea,
(2) N-(2-chlorobenzoyl)-N'-(3,5-dichloro-4-phenoxyphenyl)urea, and
(3) N-(2-chlorobenzoyl)-N'-[3,5-dichloro-4-(4-chlorophenoxy)phenyl]urea.

Examples of other insecticidally active compounds are:
(4) N-(2-chlorobenzoyl)-N'-(4-chlorophenyl)urea,
(5) N-(2-chlorobenzoyl)-N'-(4-fluorophenyl)urea,
(6) N-(2-chlorobenzoyl)-N'-(3-nitro-4-chlorophenyl)urea,
(7) N-(2-chlorobenzoyl)-N'-(4-nitrophenyl)urea,
(8) N-(2-chlorobenzoyl)-N'-(4-isopropoxyphenyl)urea,
(9) N-(2-chlorobenzoyl)-N'-(4-trifluoromethylsulphonylphenyl)urea,
(10) N-(2-chlorobenzoyl)-N'-(4-tert.-butylphenyl)urea,
(11) N-(2-chlorobenzoyl)-N'-(4-phenoxyphenyl)urea,
(12) N-(2-chlorobenzoyl)-N'-[4-(2,5-dichlorophenoxy)phenyl]urea,
(13) N-(2-chlorobenzoyl)-N'-(3-chloro-4-phenoxyphenyl)urea,
(14) N-(2-chlorobenzoyl)-N'-[4-(4-chlorophenoxy)phenyl]urea,
(15) N-(2-chlorobenzoyl)-N'-[4-(2,4-dichlorophenoxy)phenyl]urea,
(16) N-(2-chlorobenzoyl)-N'-[4-(4-chlorophenylthio)phenyl]urea,
(17) N-(2-chlorobenzoyl)-N'-[3-chloro-4-(4-chlorophenylthio)phenyl]urea,
(18) N-(2-chlorobenzoyl)-N'-[3,5-dichloro-4-(4-chlorophenylthio)phenyl]urea,
(19) N-(2-chlorobenzoyl)-N'-[4-(4-chlorophenylsulphonyl)phenyl]urea,
(20) N-(2-iodobenzoyl)-N'-(4-chlorophenyl)urea,
(21) N-(2-methylbenzoyl)-N'-(4-tert.-butylphenyl)urea,
(22) N-(2-fluorobenzoyl)-N'-(4-trifluoromethylphenyl)urea,
(23) N-(2-iodobenzoyl)-N'-(4-trifluoromethylphenyl)urea,
(24) N-(2-methylbenzoyl)-N'-(4-trifluoromethylphenyl)urea,
(25) N-(2-fluorobenzoyl)-N'-[4-(2,5-dichlorophenoxy)phenyl]urea,
(26) N-(2-fluorobenzoyl)-N'-(3-chloro-4-phenoxyphenyl)urea,
(27) N-(2-fluorobenzoyl)-N'-(3,5-dichloro-4-phenoxyphenyl)urea,
(28) N-(2-fluorobenzoyl)-N'-[3-chloro-4-(4-chlorophenylthio)phenyl]urea,
(29) N-(2-fluorobenzoyl)-N'-[3,5-dichloro-4-(4-chlorophenylthio)phenyl]urea,
(30) N-(2-chlorobenzoyl)-N'-[4-(1,2-dimethylpropyl)phenyl]urea,
(31) N-(2-chlorobenzoyl)-N'-[4-(1-adamantyl)phenyl]urea,
(32) N-(2-methylbenzoyl)-N'-(4-tert.-butoxyphenyl)urea, and
(33) N-(2-chlorobenzoyl)-N'-[4-(1,3-dimethylbutoxy)phenyl]urea.

The compounds of the invention may be used for the control of mites and insects in agriculture and horticulture, in forests and surface water, as well as for the protection of textile against attack by, for example, moths and carpet beetles, and against insects in stocks, for example in stored cereals.

The substances according to the invention may also be used for the control of insects living in the manure of warm-blooded animals, for example cows, pigs and hens. For this application the active compounds may be administered orally to the animals, for example, mixed through the food, so that they will land in the manure after some time ("through-feeding").

The compounds according to the invention are particularly active against larvae and ova of insects such as flies, mosquitos, beetles and butterflies.

In principle the compounds may be used against all insects mentioned in Pestic. Sci., 9, 373–386 (1978).

For practical applications the compounds are usually processed to form compositions. In such compositions the active substance is mixed with solid carrier material or dissolved or dispersed in liquid carrier material, if desired in combination with auxiliary substances, such as emulsifiers, wetting agents, dispersing agents and stabilisers.

Examples of compositions of the invention are aqueous solutions and dispersions, oil solutions and oil dispersions, solutions in organic solvents, pastes, dusting powders, dispersible powders, miscible oils, granules, pellets, invert emulsions, aerosol compositions and fumigating candles.

Dispersible powders, pastes and miscible oils are compositions in concentrated form which are diluted prior to or during use.

The invert emulsions and solutions in organic solvents are mainly used in air applications, namely when large areas are to be treated with a comparatively small quantity of composition. The invert emulsion may be prepared in the spraying apparatus shortly prior to or even during spraying by emulsifying water in an oil solution or an oil dispersion of the active substance. The solutions of the active substance in organic solvents may be provided with a phytotoxicity-reducing substance, for example wool fat, wool fat acid or wool fat alcohol.

In addition to the above-mentioned ingredients the compositions may also comprise other substances with properties known for such application.

For example, a lubricant such as calcium stearate or magnesium stearate, may be added to a dispersible powder or a mixture to be granulated. "Adhesives", for example polyvinyl alcohol cellulose derivatives or other colloidal materials, such as casein, may also be added for example so as to improve the adhesion of the pesticide to the crop. Furthermore, a substance may be added so as to reduce the phytotoxicity of active substance, carrier material or auxiliary material, such as wool fat or wool fat alcohol.

Known pesticidal compounds may also be incorporated in the compositions according to the invention. As a result of this the activity spectrum of the composition is widened and synergism may occur.

In addition to known acaricidal and fungicidal compounds the following known insecticidal compounds are to be considered for use in such a combination:

1. organic chlorine compounds, for example 6,7,8,9,10,10-hexachloro-1,5,5a,6,9,9a-hexahydro-6,9-methano-2,4,3-benzo[e]-dioxathiepine 3-oxide;

2. carbamates, for example 2-dimethylamino-5,6-dimethyl pyrimidin-4-yl-dmethyl carbamate and 2-isopropoxy-phenylmethylcarbamate;

3. di(m)ethyl phosphates, for example 2-chloro-2-diethylcarbamoyl-1-methylvinyl—, 2-methoxycarbonyl-1-methylvinyl—, 2-chloro-1-1(2,4-dichlorophenyl)-vinyl—, and 2-chloro-1-(2,4,5-trichlorophenyl)vinyl di(m)ethyl phosphate;

4. O,O-di(m)ethyl phosphorothioates, for example O(S)-2-methylthioethyl—, S-2-ethylsulphinylethyl—, S-2-(1-methylcarbamoylethylthio)ethyl—, O-4-bromo-2,5-dichlorophenyl—, O-3,5,6-trichloro-2-pyridyl—, O-2-isopropyl-6-methylpyrimidin-4-yl—, and O-4-nitrophenyl-O,O-di(m)-ethylphosphorothioate;

5. 0,0-di(m)ethyl phosphorodithioates, for example S-methylcarbamoylmethyl—, S-2-ethylthioethyl—, S-(3,4-dihydro-4-oxobenzo[d]-[1,2,3]-triazin-3-yl-methyl)-, S-1,2-di(ethoxycarbonyl)ethyl—, S-6-chloro-2-oxobenzooxazolin-3-ylmethyl—, and S-2,3-dihydro-5-methoxy-2-oxy-1,3,4-thiadizol-3-ylmethyl O,O-di(m)ethylphosphorodithioate;

6. phosphonates, for example dimethyl 2,2,2-trichloro-1-hydroxyethyl phosphonate.

7. natural and synthetic pyrethroids;

8. amidines, for example N'-(2-methyl-4-chlorophenyl)-N,N-dimethylformamidine; and 9. microbial insects, such as *Bacillus thuringiensis*.

The dosage of the composition of the invention desired for practical application will of course depend on various factors, for example, the application area, the active substance chosen, the form of the composition, the nature and the extent of the infestation and the weather conditions.

In general it holds that favourable results are achieved with a dose which corresponds to 10 to 5000 g of the active substance per hectare.

For the above-described "through-feeding" the active substance is mixed through the food in a quantity which is effective for insecticidal application.

The compounds according to the invention are new substances which can be prepared in a manner which is known per se for related compounds.

For example, the compounds according to the invention can be prepared by reacting a substituted amine of the general formula

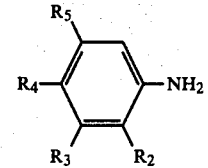

wherein $R_2$, $R_3$, $R_4$ and $R_5$ have the above-mentioned meanings, with an isocyanate of the general formula

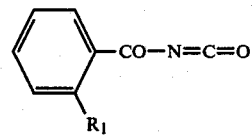

wherein $R_1$ has the meaning also stated above.

The new compounds according to the invention can also be prepared by reacting an amide of the general formula

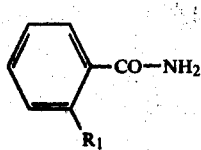

with an isocyanate of the general formula

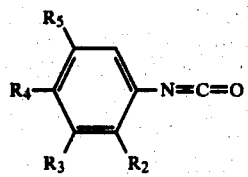

in which formulae the symbols again have the above meanings. The above reactions are carried out in the presence of a solvent, for example an aromatic hydrocarbon, an alkylhalogenide or acetonitrile, at a reaction temperature between 0° C. and the boiling point of the solvent used.

The invention will now be described in more detail with reference to the following specific examples.

EXAMPLE 1

Preparation of N-(2-chlorobenzoyl)-N'-(4-trifluoromethylphenyl)urea.

18.7 g of 2-chlorobenzoylisocyanate were added to 150 ml of a solution of 17.7 g of 4-trifluoromethylaniline in dry acetonitrile. After stirring at room temperature for a few hours, the crystalline precipitate was sucked off, washed with successively acetonitrile, ethanol and petroleum ether and dried in air. The desired product was obtained in a yield of 29.0 g; melting point 214° C.

In a corresponding manner in which, if desired, dry diethyl ether was used as a solvent instead of acetonitrile, the following compounds were prepared: the numbers of the compounds correspond to the numbers used before in this specification.

| compound no. | melting point | compound no. | melting point |
|---|---|---|---|
| (2) | 190° C. | (18) | 170–174° C. |
| (3) | 205–206° C. | (19) | 230–235° C. |
| (4) | 202° C. | (20) | 212° C. |
| (5) | 182° C. | (21) | 167,5° C. |
| (6) | 188° C. | (22) | 206° C. |
| (7) | 253° C. | (23) | 208° C. |
| (8) | 167–167,5° C. | (24) | 181° C. |
| (9) | 225° C. | (25) | 170–177° C. |
| (10) | 175° C. | (26) | 172° C. |
| (11) | 169° C. | (27) | 167° C. |
| (12) | 187,5° C. | (28) | 173–174° C. |
| (13) | 173° C. | (29) | 187,5° C. |
| (14) | 220° C. | (30) | 140,5° C. |
| (15) | 206–209° C. | (31) | 260° C. |
| (16) | 181–184° C. | (32) | 154° C. |
| (17) | 210,5–211° C. | (33) | 118–120° C. |

EXAMPLE 2

The compositions of the invention are prepared by suspending the compounds in water in the presence of a dispersing agent, for example, lignin sulphonate, and/or a wetting agent, for example naphthalene sulphonate, an alkylsulphate, an alkylbenzenesulphonate, an alkylpolyoxyethylene or an alkylarylpolyoxyethylene; in a specific example a mixture of lignin sulphonate and naphthalene sulphonate is used.

Young plants of Brussels sprouts, approximately 15 cm high, are sprayed with the compositions thus obtained in various concentrations. After the plants have dried up they are placed in transparent plastic cylinders and then infected with 5 larvae of Pieris brassicae (caterpillars of the cabbage white butterfly). The cylinders are then covered with a gauze and stored, an alternating light-dark cycle of 18 hours light and 6 hours dark being used; temperature in the light 24° C., relative humidity (RV) 70%, temperature in the dark 19° C., 80–90%, RV. After 5 days the mortality percentage of the larvae is established. Each experiment is carried out threefold. The results of the experiments are stated in the Table A below. The meanings of the symbols stated in the table are as follows:

+ = 90–100% mortality
± = 50–90% mortality
− = <50% mortality

TABLE A

| | Insecticidal activity against larvae of Pieris brassica | | | | | | | |
|---|---|---|---|---|---|---|---|---|
| compound no. | activity; conc. in mg of active substance per liter | | | | | | | |
| | 300 | 100 | 30 | 10 | 3 | 1 | 0,3 | 0,1 |
| (1) | + | + | + | + | + | + | + | ± |
| (2) | + | + | + | + | + | ± | − | |
| (3) | + | + | + | + | + | + | + | − |
| (4) | + | + | + | + | + | + | − | |
| (5) | + | + | + | + | + | + | − | |
| (6) | + | + | + | − | | | | |
| (7) | + | + | + | + | ± | − | | |
| (8) | + | + | + | − | | | | |
| (9) | + | + | + | + | − | | | |
| (10) | + | + | + | + | + | + | ± | − |
| (11) | + | + | + | + | + | − | | |
| (12) | + | + | + | + | + | ± | − | |
| (13) | + | + | + | + | + | ± | − | |
| (14) | + | + | + | + | ± | − | | |
| (15) | + | + | + | + | + | − | | |
| (16) | + | + | + | + | + | − | | |
| (17) | + | + | + | + | + | − | | |
| (18) | + | + | + | + | + | − | | |
| (19) | + | + | + | + | + | + | − | |
| (20) | + | + | + | + | ± | − | | |
| (21) | + | + | + | + | + | ± | − | |
| (22) | + | + | + | ± | − | | | |
| (23) | + | + | + | + | + | + | − | |
| (24) | + | + | + | + | ± | − | | |
| (25) | + | + | + | + | ± | − | | |
| (26) | + | + | + | + | − | | | |
| (27) | + | + | + | + | ± | − | | |
| (28) | + | + | + | + | − | | | |
| (29) | + | + | + | + | + | + | − | |
| (30) | + | + | + | + | ± | − | | |
| (31) | + | + | + | − | | | | |
| (32) | + | + | + | + | − | | | |
| (33) | + | + | + | + | ± | − | | |

EXAMPLE 3

Young potato plants, approximately 15 cm high, are sprayed with the compositions obtained according to example 2 in various concentrations. After the plants have dried up, cylinders of transparent plastics are placed over the plants. The plants are then infected with 10 larvae of Leptinotarsa decemlineata (larvae of the colorado beetle) and stored as indicated in example 2. After 5 days the mortality percentage of the larvae is established. The results of the experiment are recorded in table B below. The meanings of the symbols are the same as in example 2.

TABLE B

Insecticidal activity against larvae of *Leptinotarsa decemlineata*

| compound no. | activity; conc. in mg of active substance per liter | | | | | | |
|---|---|---|---|---|---|---|---|
| | 300 | 100 | 30 | 10 | 3 | 1 | 0,3 |
| (1) | + | + | ± | ± | − | | |
| (2) | + | + | + | + | ± | − | |
| (3) | + | + | + | + | + | ± | − |
| (4) | + | + | ± | − | | | |
| (5) | ± | ± | − | | | | |
| (6) | + | + | + | ± | − | | |
| (8) | ± | ± | − | | | | |
| (10) | + | + | ± | − | | | |
| (11) | + | + | + | − | | | |
| (17) | + | ± | − | | | | |
| (18) | + | + | ± | − | | | |
| (19) | + | ± | − | | | | |
| (21) | + | + | − | | | | |
| (22) | ± | − | | | | | |
| (23) | + | + | + | − | | | |
| (24) | + | + | + | ± | − | | |
| (27) | + | + | + | ± | − | | |
| (30) | ± | ± | − | | | | |
| (33) | + | + | + | + | ± | − | |

What is claimed is:

1. The compound N-(2-chlorobenzoyl)-N'-(4-trifluoromethylphenyl)-urea.

2. An insecticidal composition comprising
   an insecticidally effective amount of N-(2-chlorobenzoyl)-N'-(4-trifluoromethylphenyl)urea and
   a liquid or solid inert pesticide carrier.

3. A method of controlling insects comprising
   applying to said insects or to insect infected areas the insecticidal composition of claim 2 in a dosage of about 10 to about 5,000 g of active substance per hectare.

* * * * *

UNITED STATES PATENT AND TRADEMARK OFFICE
CERTIFICATE OF CORRECTION

PATENT NO. : 4,399,152
DATED : August 16, 1983
INVENTOR(S) : Marius S. BROUWER, et al.

It is certified that error appears in the above-identified patent and that said Letters Patent is hereby corrected as shown below:

Please make the following corrections in the heading of the Patent:

"[73] Assignee:   Duphar International B.V.," to

-- [73] Assignee:   Duphar International Research B.V.,--.

"[56]  3,989,847 11/1976 Wellinga et al. .......424/322"
should be -- 3,989,842  11/1976 Wellinga et al. .....424/322 --.

Signed and Sealed this

Fifth Day of March 1985

[SEAL]

Attest:

DONALD J. QUIGG

Attesting Officer   Acting Commissioner of Patents and Trademarks